(12) United States Patent
Rasmussen

(10) Patent No.: US 10,716,870 B2
(45) Date of Patent: Jul. 21, 2020

(54) FACILITY, AN UNMANNED VEHICLE AND METHOD FOR PROCESSING OF DIRTY SURGICAL INSTRUMENTS

(71) Applicant: KEN HYGIENE SYSTEMS A/S, Broby (DK)

(72) Inventor: Kim Rasmussen, Svendborg (DK)

(73) Assignee: KEN HYGIENE SYSTEMS A/S, Broby (DK)

( * ) Notice: Subject to any disclaimer, the term of this patent is extended or adjusted under 35 U.S.C. 154(b) by 176 days.

(21) Appl. No.: 15/773,939

(22) PCT Filed: Nov. 4, 2016

(86) PCT No.: PCT/EP2016/076728
§ 371 (c)(1),
(2) Date: May 4, 2018

(87) PCT Pub. No.: WO2017/077073
PCT Pub. Date: May 11, 2017

(65) Prior Publication Data
US 2018/0318458 A1 Nov. 8, 2018

(30) Foreign Application Priority Data
Nov. 6, 2015 (EP) .................................. 15193473

(51) Int. Cl.
*A61L 2/00* (2006.01)
*A61B 1/00* (2006.01)
(Continued)

(52) U.S. Cl.
CPC ................ *A61L 2/26* (2013.01); *A61B 50/10* (2016.02); *A61B 50/13* (2016.02); *A61B 50/33* (2016.02);
(Continued)

(58) Field of Classification Search
CPC ........ A61L 2/00; A61L 2/0029; A61L 2/0082; A61L 2/10; A61L 2/16; A61L 2/20; A61L 2202/24
(Continued)

(56) References Cited

U.S. PATENT DOCUMENTS 5,511,594 A 4/1996 Brennan et al.

FOREIGN PATENT DOCUMENTS

DE 20023832 U1 10/2006
EP 0994731 B1 12/2002
(Continued)

OTHER PUBLICATIONS

International Search Report and Written Opinion for PCT/EP2016/076728, dated Mar. 13, 2017.
(Continued)

*Primary Examiner* — Monzer R Chorbaji
(74) *Attorney, Agent, or Firm* — Brinks Gilson & Lione; John C. Freeman

(57) ABSTRACT

The invention relates to a facility which has a dirty facility area and an adjacent clean facility area, baskets for receiving the dirty articles, and a wall separating the dirty area from the clean area, the dirty area including an entry door for receiving the dirty articles, pre-processing stations with tables for the pre-washing and/or sorting by a human operator, or even by a robotic operator, of the dirty articles and for arranging the pre-washed and/or sorted articles in the baskets, pick-up points at the pre-processing stations for pick-up of the baskets with the pre-washed and/or sorted articles, a plurality of washers, eg. machines operating in a manner similar to a dishwasher, positioned along the dividing wall, for washing the pre-washed and/or sorted articles arranged in the baskets, the washers having an inlet opening in the dirty area and an outlet opening for washed articles in the
(Continued)

clean area, the clean area including processing stations with tables for processing by a human operator, or even a robotic operator, of the washed articles. One or more unmanned vehicles are configured for travelling on the floor of the dirty area at least between pick-up points and an inlet opening of the respective washers, each vehicle including a base with a front end and a rear end, an upper part with a loading platform configured for supporting the baskets, an on-board control device for receiving and executing mission information, each pre-processing station including a first type control device for direct or indirect communication with one or more of the vehicles each washer including a respective second type control device for direct or indirect communication with the one or more vehicles and/or for direct or indirect communication with the first control devices, each first control device being for calling a vehicle to the pick-up point and/or for dispatching a vehicle from the pick-up point.

11 Claims, 10 Drawing Sheets

(51) Int. Cl.
| | | |
|---|---|---|
| *B08B 7/00* | (2006.01) | |
| *B08B 9/00* | (2006.01) | |
| *B08B 3/00* | (2006.01) | |
| *A61L 2/26* | (2006.01) | |
| *B08B 13/00* | (2006.01) | |
| *A61B 50/13* | (2016.01) | |
| *A61B 50/33* | (2016.01) | |
| *A61B 50/34* | (2016.01) | |
| *A61B 50/10* | (2016.01) | |

(52) U.S. Cl.
CPC .............. *A61B 50/34* (2016.02); *B08B 13/00* (2013.01); *A61L 2202/14* (2013.01); *A61L 2202/16* (2013.01); *A61L 2202/24* (2013.01)

(58) Field of Classification Search
USPC ..... 422/1, 24, 28, 292, 300; 134/6, 22.1, 44, 134/61; 600/133
See application file for complete search history.

(56) References Cited

FOREIGN PATENT DOCUMENTS

| EP | 1787731 A2 | 5/2007 | |
|---|---|---|---|
| EP | 1787731 A3 | 3/2008 | |
| WO | 0134015 A1 | 5/2001 | |
| WO | WO 01/34015 A1 * | 5/2001 | ............. A47L 15/36 |
| WO | 2007000639 A1 | 1/2007 | |
| WO | 2014036217 A2 | 3/2014 | |

OTHER PUBLICATIONS

Preliminary Report on Patentability for PCT/EP2016/076728, dated Jan. 31, 2018.

* cited by examiner

FACILITY, AN UNMANNED VEHICLE AND METHOD FOR PROCESSING OF DIRTY SURGICAL INSTRUMENTS

RELATED APPLICATIONS

This application claims the benefit under 35 U.S.C. § 371 of the filing date of International Patent Application No. PCT/EP2016/076728, having an international filing date of Nov. 4, 2016, which claims priority to European Application No. 15193473.4, filed Nov. 6, 2015, the contents of both of which are incorporated herein by reference in their entirety.

TECHNICAL FIELD

The present invention relates to a facility, a vehicle and method for the processing of dirty surgical instruments and the like articles used in hospitals.

BACKGROUND OF THE INVENTION

Used surgical instruments and related medical devices are typically handled by a Central Clean Instrument Supply (hereafter "CCIS")-department or facility (sometimes also referred to as a Central Sterile Services Department) within a hospital or other related medical service facility. The CCIS-department processes the used surgical instruments and other types of re-usable medical devices to bring them from a "dirty" or contaminated state to a washed/disinfected state. For this purpose the CCIS-department is divided into a dirty/unclean area separated physically from a clean area.

Elements of the CCIS-department processes may be summarized chronologically as follows:
 i. in the dirty area, trays with dirty medical devices are received in containers or the like from the operating rooms;
 ii. the trays are unloaded;
 iii. the instruments are identified;
 iv. the instruments are pre-cleaned or prepared by hand;
 v. the instruments are arranged on washer trays,
 vi. the washer trays are arranged on a washer rack or basket so the instruments can be properly cleaned in a washer sized to receive the basket;
 vii. the washer basket with instruments is passed through a pass-through washer/disinfector to the clean area;
 viii. the instruments are inspected for cleanliness in the clean area; and
 ix. the washer baskets, and possibly also the washer trays, are returned to the dirty area.

As will be understood, after a surgical procedure, dirty instruments are normally sent to the CCIS-department with the intention of washing/disinfecting and repackaging them for future use, possibly even with a sterilization step.

More specifically, the first step in the washing/disinfection process is decontamination where a CCIS-department worker opens a container and finds a tray with dirty, disorganized instruments/articles. Each instrument is then manually washed or scrubbed. The purpose of this manual process is to physically remove deposits and to break up biofilms such as dried blood that may be adherent to the instruments. The instruments/articles are then placed on trays which are put on cage-like baskets, and are then run through the pass-through washer/disinfector having an entry opening in the dirty area and an exit opening in the clean area, and which essentially operates as a dishwasher wherein the articles carried by the baskets are cleaned by water impingement and detergent. Typically, the baskets have a rotating spray bar connected to a water supply in the washer and which emits high pressure water and detergent spray to clean the instruments by impingement of the water jets on the instrument surfaces. In alternative operations the articles may be placed directly on grid-like shelfs integral with the baskets.

When the instruments leave the washer/disinfector, they are considered decontaminated. Further processing continues in the "clean" area of CCIS-department. Here the instruments are inspected, counted, sorted, and repacked; this may be carried out by a robot.

Components of a prior art CCIS-department or facility as described are outlined in the preamble of claim 1, whereby the facility has a dirty facility area and an adjacent clean facility area, baskets for receiving the dirty articles, and a wall separating the dirty area from the clean area, the dirty area including an entry door for receiving the dirty articles, pre-processing stations with tables, for pre-processing the dirty articles for the subsequent washing—such as through a pre-washing and/or sorting by a human operator, or even by a robotic operator—and for arranging the thus pre-treated articles in the baskets, pick-up points at the pre-processing stations for pick-up of the baskets with the pre-processed (eg. pre-washed and/or sorted articles), a washer, eg. machine operating in a manner similar to a dishwasher, positioned along the dividing wall, for washing the pre-processed (eg. pre-washed and/or sorted) articles arranged in the baskets, the washer having a chamber with an inlet opening in the dirty area and an outlet opening for washed articles in the clean area, the clean area including processing stations with tables for processing by a human operator, or even a robotic operator, of the washed articles. Washers as referred to are also sometimes known as "washer-disinfectors". The pre-processing mentioned above may in some cases simply involve a manual preparing of the articles for the subsequent washing, including by way of example an opening of scissors to expose all surfaces thereof to the detergent used in the pashing in the washer.

EP 994 731 shows a CCIS-department or facility and method for the processing of used surgical instruments and other types of re-usable medical devices arriving from an operating room or other clinical facility. Trays with such instruments are delivered to the "dirty" side or area of CCIS-department, where the instruments are unloaded from the trays, hand washed and then placed on trays taken to a conveyor that runs in front of and alongside with a plurality of washers/cleaning units each having a chamber. Mechanisms are provided for loading the trays into the washers using a plurality of individual mechanical loaders; in the clean area a similar conveyor is provided alongside the washers, with individual mechanical unloaders or extractors for extracting the trays from the washer chambers onto the conveyor. When it is necessary to perform routine maintenance or repair on one of the washers it is necessary for a maintenance person to enter either the dirty area or the clean area in order to service the washer. In either case the presence of the maintenance person in either the dirty area or the clean area will interfere with the normal progress of activities in these areas since the conveyor placed alongside the washers must be removed for him to obtain access to the particular washer which is to be serviced. In the prior art there is no automated facility or method which avoids interruption of the normal operation of such automated washer facilities when maintenance is carried out.

EP 1 787 731 discloses a facility including a row of washers and a trolley moving back and forth along the washers, along a predetermined path defined by a track.

SUMMARY OF THE INVENTION

It is one object of the present invention to provide a more efficient facility for the processing of used surgical instruments and related medical devices, such as in a Central Clean Instrument Supply (CCIS)-department. A further object of the present invention is to provide such a facility in which a reduced floor area is required, in at least the dirty area or the clean area.

It is another object of the present invention to provide a washer/disinfecting facility in which the components requiring access for maintenance are accessible without disruption of the entire facility.

The above object are fulfilled with a facility as defined in the characterising clause of claim 1 whereby one or more unmanned vehicles are configured for travelling on the floor of the dirty area at least between pick-up points and an inlet opening of the respective washer(s), each vehicle including a base with a front end and a rear end, an upper part with a loading platform configured for supporting the baskets, and an on-board control device for receiving and executing mission information, each pre-processing station including a first type control device for direct or indirect communication with one or more of the vehicles, each washer including a respective second type control device for direct or indirect communication with the one or more vehicles and/or for direct or indirect communication with the first control devices, each first control device being for calling a vehicle to the pick-up point and/or for dispatching a vehicle from the pick-up point. While often the washers are placed adjacent each other, in alignment with each other and with the wall being straight, it will be understood that other layouts may be contemplated wherein the wall has a eg. a meandering outline with the inlet openings of the washers located offset with respect to each other.

In one embodiment one or more additional vehicles, not belonging to the group of vehicles travelling in the dirty area but similar or identical in structure, are configured for travelling on the floor of the clean area at least between the washer outlet opening for cleaned articles and the processing stations for the washed articles.

Preferably, the base of the unmanned wheeled vehicles have a size in the order of (length×width×height) 1 m×0.5 m×0.5 m, making them convenient for travel in facilities of the stated nature. Preferably, each of the vehicles include sensors for detecting obstacles along the path of movement across the floor(s); the sensors may in one embodiment only be located at a front end.

Each vehicle preferably carries a shifting device for engaging a respective basket and for moving the basket in directions to and from said vehicle, whereby human operators in the facility are not required to perform this operation. By carrying such a device on-board the vehicles, need for placing individual, fixed basket shifting devices at each pre-processing station is avoided, reducing costs. By configuring the shifting device such that loading/unloading takes place at the aforementioned front end having obstacle detecting sensors, applying such sensors, or sensors having the same degree of accuracy, at the rear end may be avoided since the vehicles may then be configured to drive only, or primarily, forwardly towards all loading/unloading stations.

Preferably, the basket shifting device is located on the upper part of the vehicles, allowing the upper part to be manufactured separately, and to be mounted onto a standardised base of such unmanned vehicles, which base may then be configured to include sensitive electronics components, such as batteries providing propulsion energy for the vehicles as well as energy for driving the shifting device and other mechanical components, such as an actuator, such as a scissor mechanism, for moving the upper part up and down with respect to the base. The possibility for such an up/down movement allows the vehicle to operate between locations where the loading platform of the upper part must be positioned level with different surfaces. By way of example, the level at which the baskets must be inserted into the washers may be different from the level of the surface of tables defining the pre-processing stations.

Preferably, the shifting device is configured for moving the baskets completely onto and off the vehicle platform. Where the basket must be positioned relatively deep inside the washers to allow for a washer door to close, this shifting device carried on-board each vehicle ensures correct positioning of the basket by being extendable to such a length from the vehicles that the baskets, possibly supported by a bridging ramp, can be fully inserted/pushed into the washers whereupon the washer door can be closed and the washing cycle be initiated, after retraction of the shifting device out of the washer. A similar shifting device applied to the vehicle operating in the clean area allows for the baskets carrying the washed articles to be withdrawn from a position deep inside the washer.

A method of operating the facility is also disclosed and claimed herein whereby a human operator inputs a requests into the first type control device arranged at a pre-processing station such as to summon one of the vehicles in the dirty area to arrive into a position at an adjacent one of the pick-up points, eg. adjacent to the station where operator is working, whereby data representing information about the status of the washing cycle carried out by the respective washers is received, whereby there is a shifting of a basket containing the articles to be washed to the platform of the vehicle arrived at the pick-up point, and where this vehicle is directed towards the washer which is either ready to receive a basket for washing the articles therein, or which first will be ready to receive a basket.

DETAILED DESCRIPTION

The invention will now be explained in more details below by means of examples of embodiments with reference to the schematic drawings.

Figure 1A:
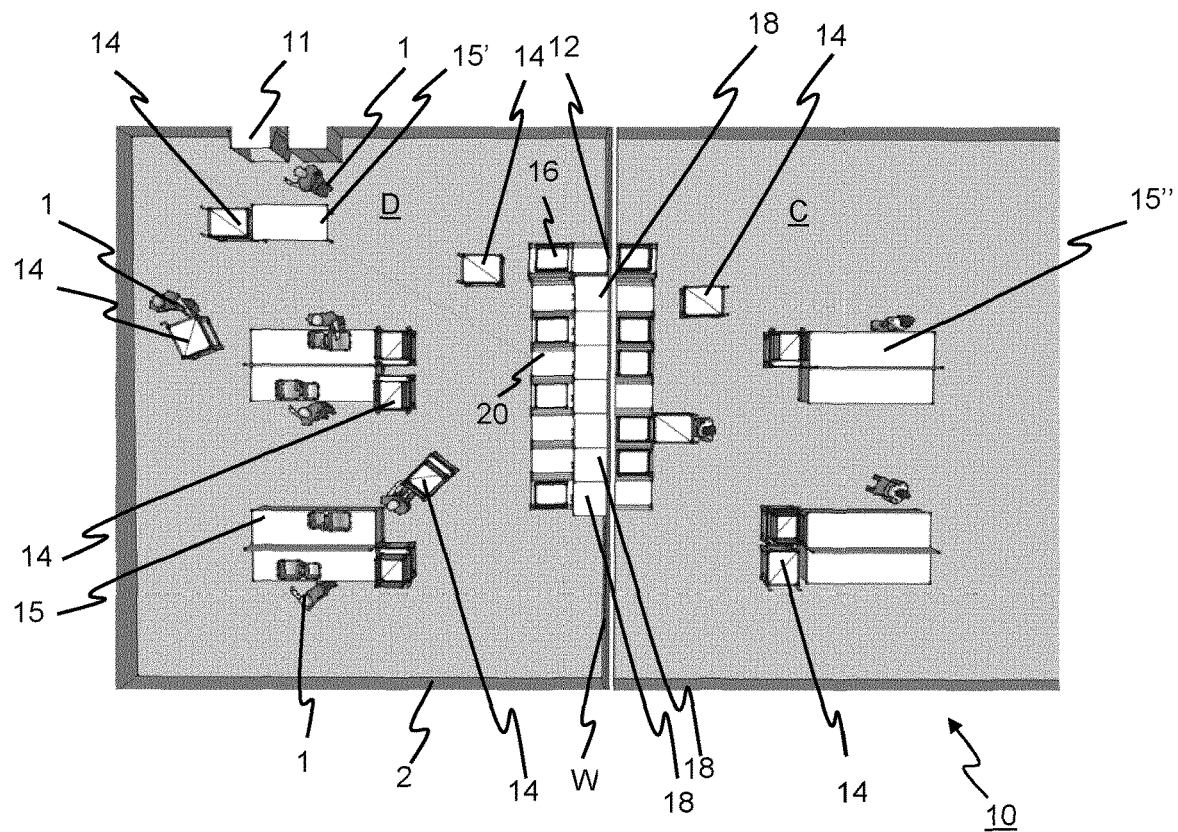
FIGS. 1a-1c show a prior art facility, seen from above and in perspective views showing in particular the clean area and the dirty area, respectively.
Figure 1B:
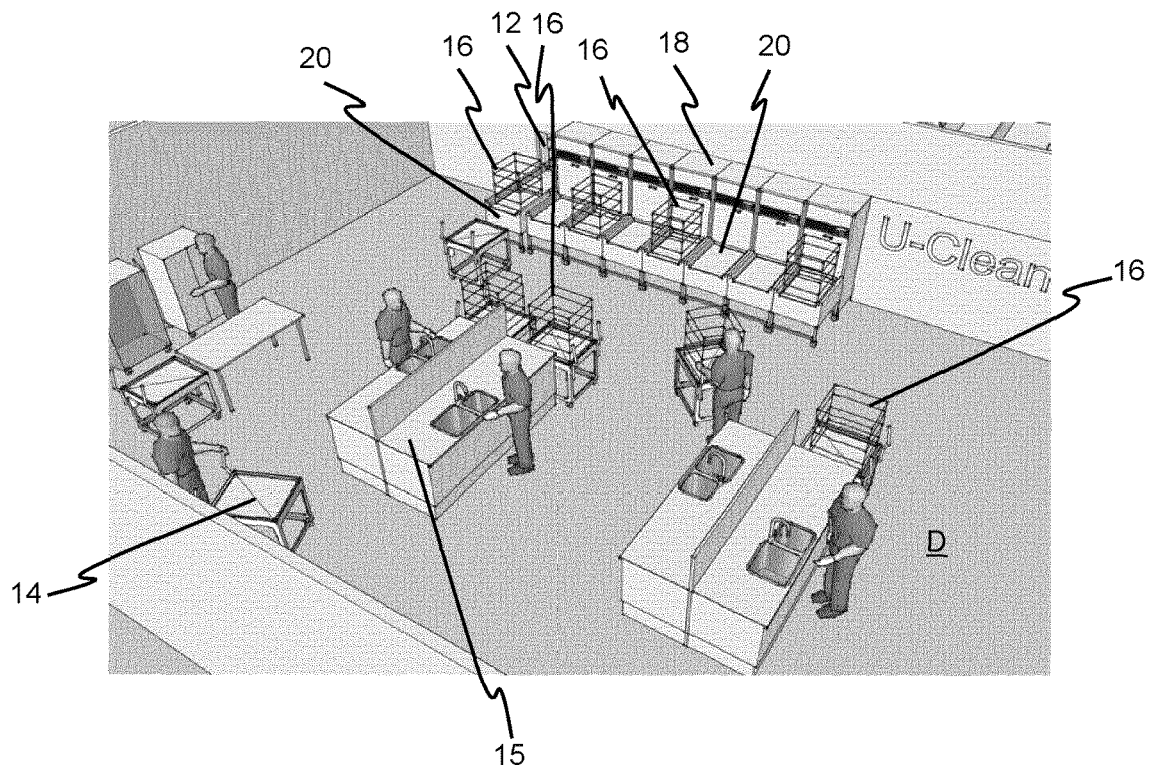
Figure 1C:
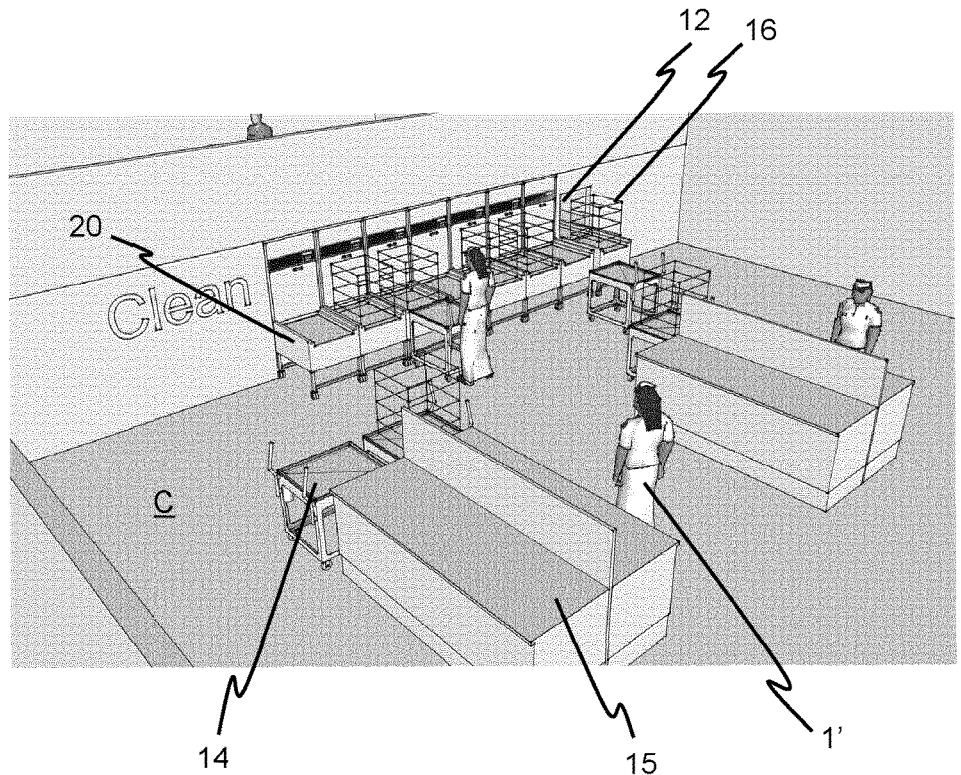

FIGS. 1a-1c show a prior art facility or department 10 and method for cleaning articles in the form of dirty medical articles/instruments, comprising a plurality of pass-through washers 18 arranged in a row next to each other. More specifically, FIG. 1a shows seen from above the general outline of a known Central Clean Instrument Supply (CCIS)-department with the various components defining the facility 10. The facility 10 comprises seven washers 18, each of which may be arranged for processing a different type of medical instrument. That is, one washer 18 may be arranged for processing respiratory therapy equipment, and another may be arranged for processing instruments used in laparoscopic surgery. Still another of the washers 18 in the facility 10 may be arranged for processing flexible fiber optic scopes. Normally, however, the washers 18 are used without considering the contents of the baskets 16.

The washers 18 each comprise two doors; a loading door facing the dirty area D of the washer and an extraction door facing the clean area C of the department/facility 10. The loading and extraction doors are, in a preferred embodiment, slidably operable and provide for the insertion into or extraction from a washing chamber of the washer 18 of a basket or rack 16 with a rotating spray bar, formed as an open cage and bearing instruments to be cleaned/washed. The instruments may comprise, for example, surgical instruments, hollowware, trays, anaesthetic equipment, rigid endoscopes and laboratory glassware. Any suitable washer can be utilised; suitable washers of the pass-through type can be obtained from, for example, KEN A/S.

The department or facility 10, generally surrounded by wall 2 is divided by a partition or wall W into the dirty area D separated from the clean area C. An entry door 11 allows for operators 1 and dirty articles A carried in containers to enter the dirty area D; a passage 12 allows for clean baskets 16 to re-enter the dirty area from the adjacent clean area C, after having passed through the washers 18.

As shown, each area has a number of processing stations in the form of tables 15, each with a wash basin/sink and allocated to a respective human operator/worker 1. Each worker 1 has a wheeled trolley or cart 14 used for moving the aforementioned containers across the floor from a receiving table 15' at the entry door 11 to the table 15 allocated to the worker/operator 1. At his table 15 the worker 1 sorts or groups the articles after a manual washing/scrubbing in the sink to physically remove deposits and to break up biofilms such as dried blood that may be adherent to the instruments/articles. The worker 1 then places each group or category of instrument on a corresponding tray (not shown) which is then placed at a desired level in a basket or rack 16 of cage-structure sitting on a cart 14. After filling the basket 16 the worker wheels the cart 14 towards a washer 18, as best seen in FIG. 1b, pushes the rack basket onto a platform 20 in a holding bay in front of a washer 18. When the washer 18 has finished a washing programme and is ready to receive a new batch for washing, a mechanical transferring device may automatically transfer the basket 16 on the associated platform 20 into the washer 18, following which washing of the articles in the basket 16 is initiated. This procedure is routinely followed by all workers 1 in the dirty area D.

In the clean area C, on the other hand, baskets 16 with washed articles are transferred automatically mechanically from the extraction doors of the washers 18 to platforms 20 and then to carts 14 operated by workers 1' that carry out a packaging of the washed articles, or arrange for a further treatment, such as a sterilizing, as shown in FIG. 1c. Empty baskets are returned via passage 12.

Figure 2A:
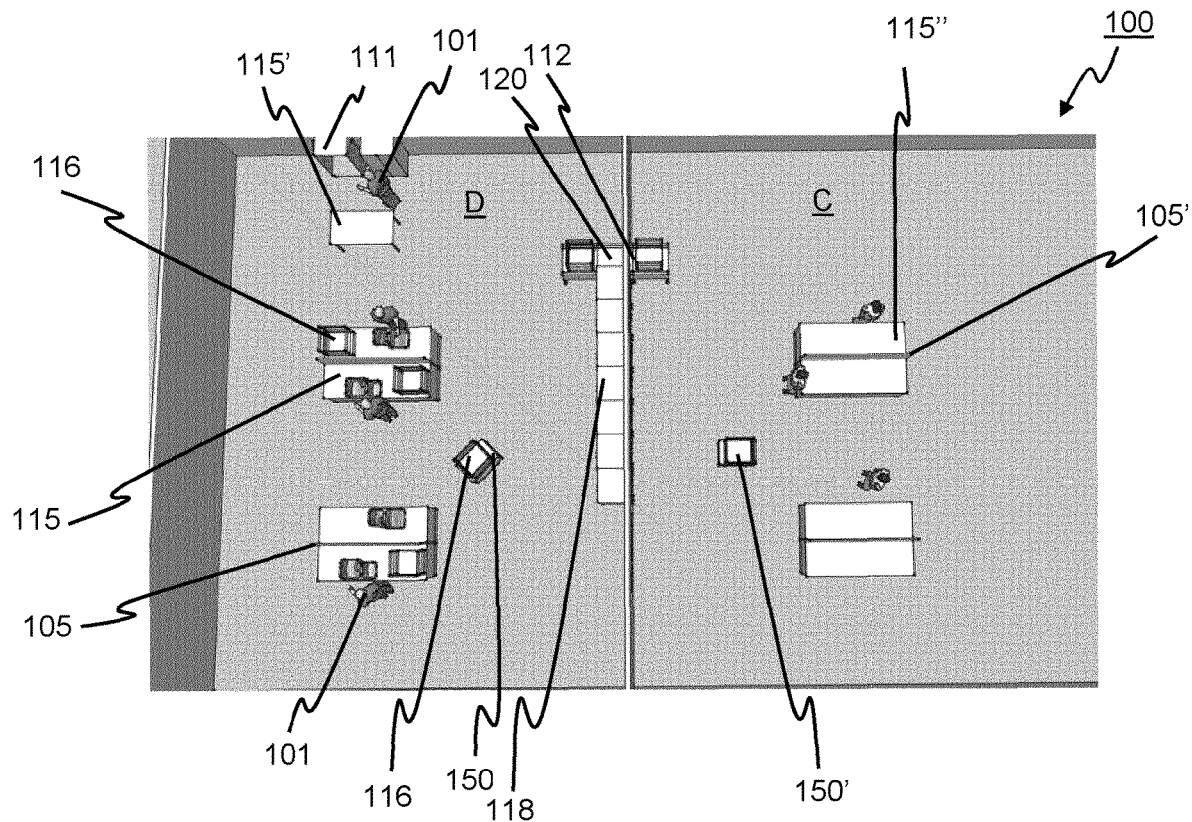
FIGS. 2a-2c show an embodiment of the facility of the invention, seen from above and in perspective views showing in particular the clean area and the dirty area, respectively.
Figure 2B:
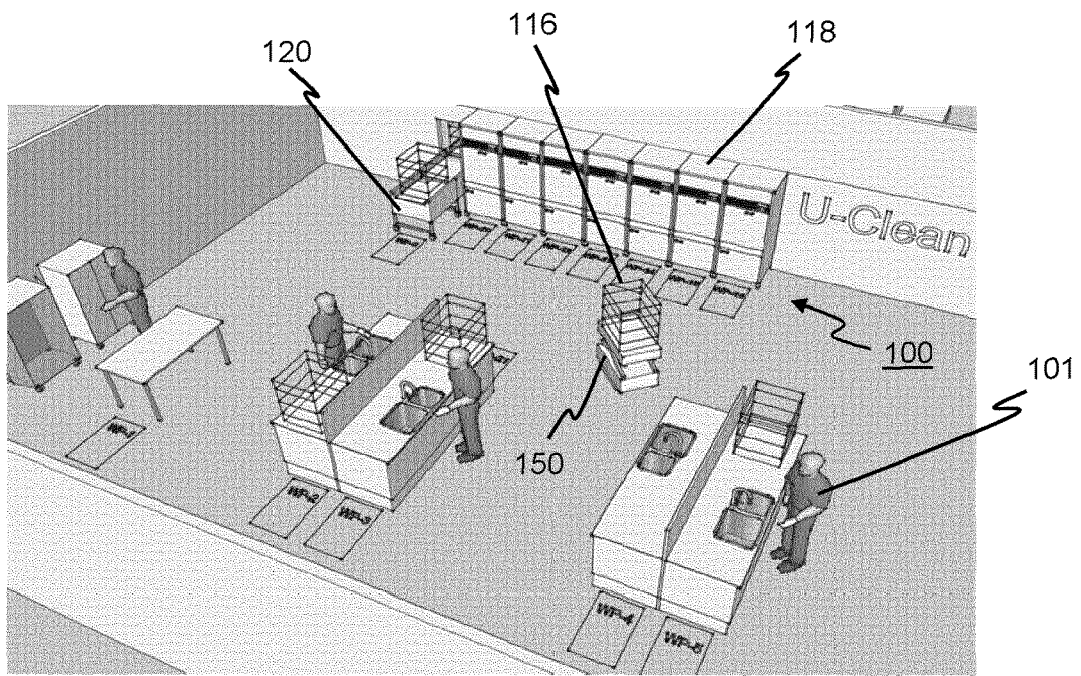
Figure 2C:
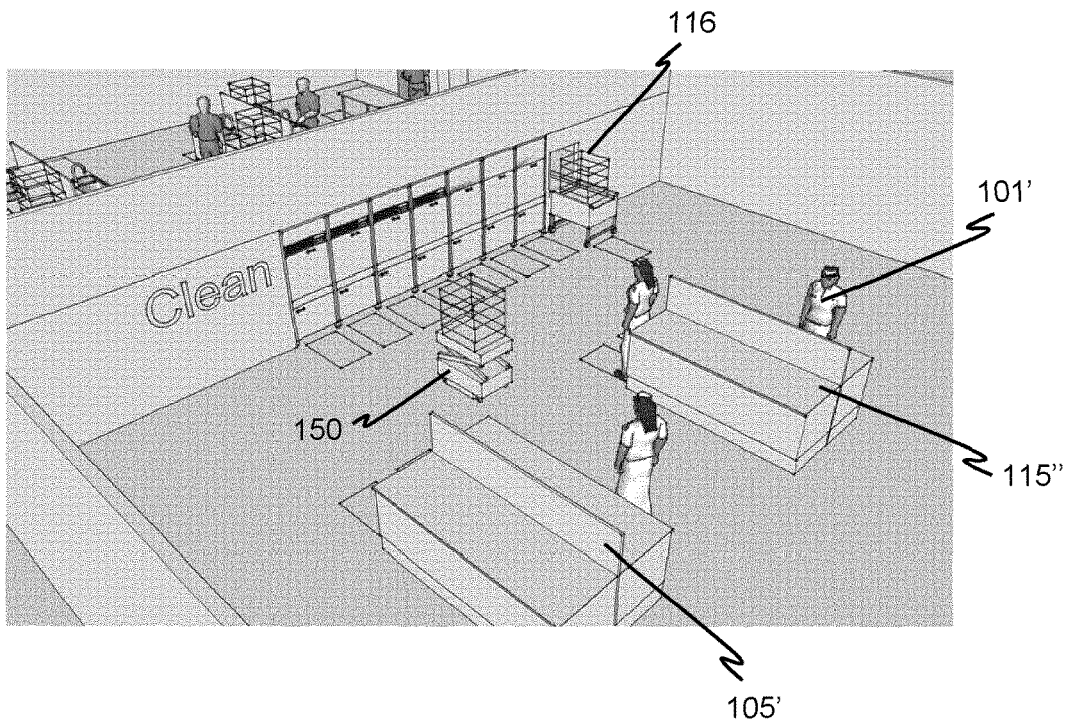

FIGS. 2a-c show a facility 100 in accordance with an embodiment of the present invention, for cleaning articles as referred to above and comprising a plurality of washers 118. In principle the facility 100 may have an outline as described above; components similar or identical to those of the prior art facility 10 are referred to below are shown by same number, increased by 100. Human operators are identified by numeral 101.

Figure 3A:
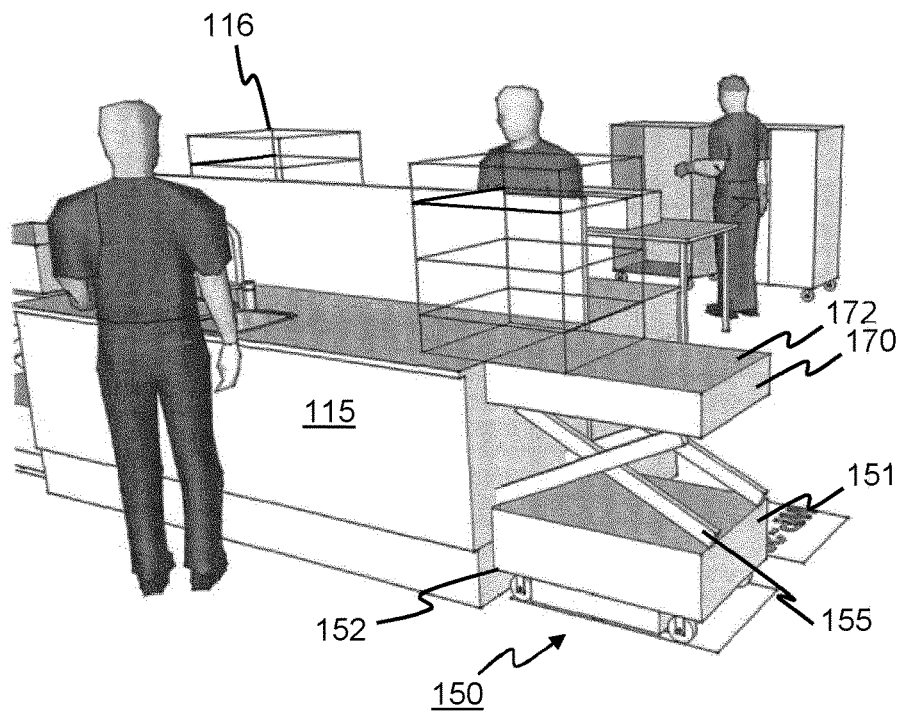
FIGS. 3a-3c show various pick-up points or unloading points in the clean area and in the dirty area.
Figure 4A:
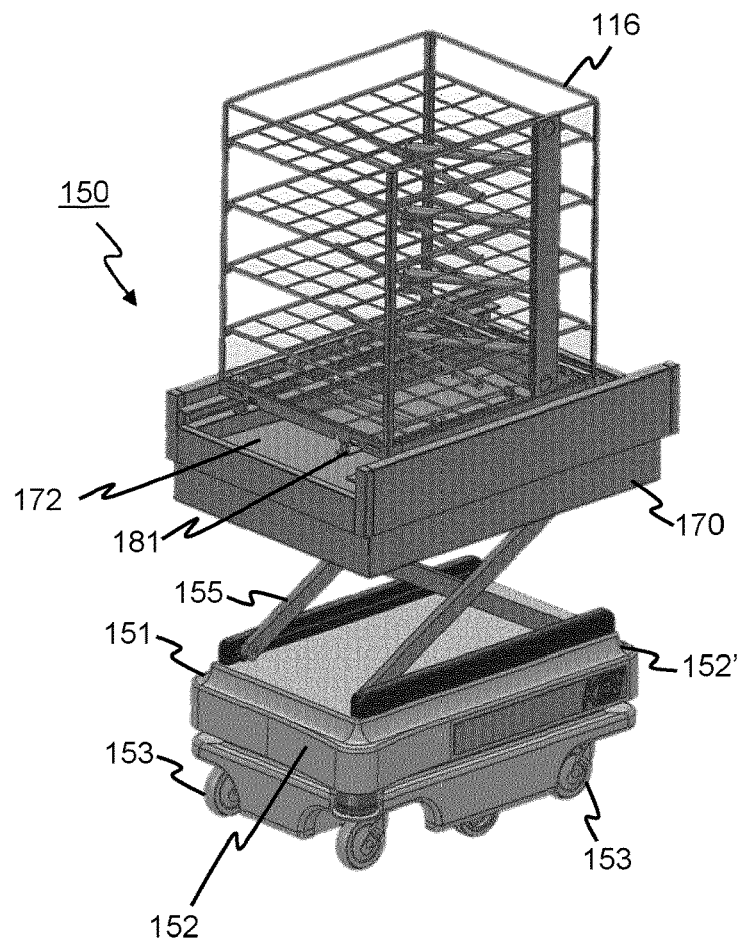
FIGS. 4a and 4b show an embodiment of a vehicle part of the facility and carrying a basket, in the process of loading/unloading the basket.

The novel facility 100 of the present invention comprises a number of wheeled unmanned vehicles 150 configured for travelling on the floor of the facility—normally with several in the clean area C and several in the dirty area D—and which preferably each have a set of sensors in order to avoid striking any obstacles. As shown in FIG. 3a, each vehicle 150 has a base 151 with wheels 153 and a front end 152 and a rear end, and an upper part 170 with a loading platform structure 172 including a loading platform pan 172' configured for supporting a basket 116; preferably, an actuator, such as an actuator driving a scissor mechanism 155 or controlling vertically telescoping bars, is incorporated for moving the upper part 170 vertically with respect to the base 151. Moreover, each vehicle 150 carries a basket shifting device 180, discussed below with reference to FIG. 4a, for engaging a respective basket 116 and for moving the basket 116 generally horizontally in directions to and from the vehicle 150, the shifting device preferably being located on the upper part 170.

The vehicles 150 are each provided with the aforementioned sensors at least at the front end 152 thereof (see FIG. 3a) and carry an on-board control device OBCD for receiving and executing mission information, i.e. information about a path, normally a two-dimensional path, along which the vehicle 150 should move, such as within a digital map representing a facility floor plan similar to that of FIG. 2a, as well as data representing operation of the basket shifting device described further below.

Movement of the vehicle 150 is initiated inter alia following requests by the operators 101 inputting requests into data panels 105 arranged at each processing station or table 115. One typical request would be to summon a vehicle 150 to arrive into a position at a pick-up point WP-x, with front end 152 against the table 115, as shown in FIG. 3a, where the upper part 170 is raised to a position with the supporting surface defined by the pan 172' of the loading platform structure 172 being level with the surface of table 115 and where the basket shifting device (not shown in FIG. 3a) engages the filled basket 116 to pull it from the table 115 and slide it completely into a position supported fully and stable by the loading platform structure 172.

From each washer 118 the vehicle 150 receives data, directly or indirectly via a main control unit, preferably by wireless communication and preferably continuously, representing information about the status of the washing cycle carried out by the respective washer 118. Based on this information the on-board control device OBCD directs, or is instructed to direct, the vehicle 150 across the floor towards a washer 180 which is either ready to receive the basket 116, or which first will be ready to receive the basket 116, following which the vehicle 150 moves to the position shown in FIG. 3b in front of that washer 118. When the washer 118 is ready to receive the basket 116 the basket shifting device of the vehicle 150 engages the basket 116 and pushes it off the loading platform structure 172, preferably fully into correct position inside the washer 118 such that standard washers 118 without any basket shifting capability may be used. While the basket shifting device could operate as a crane lifting the basket 116 rather than just sliding it off the vehicle 150, this is not preferred due to the relatively high loads such a solution would put on a crane.

Figure 3B:
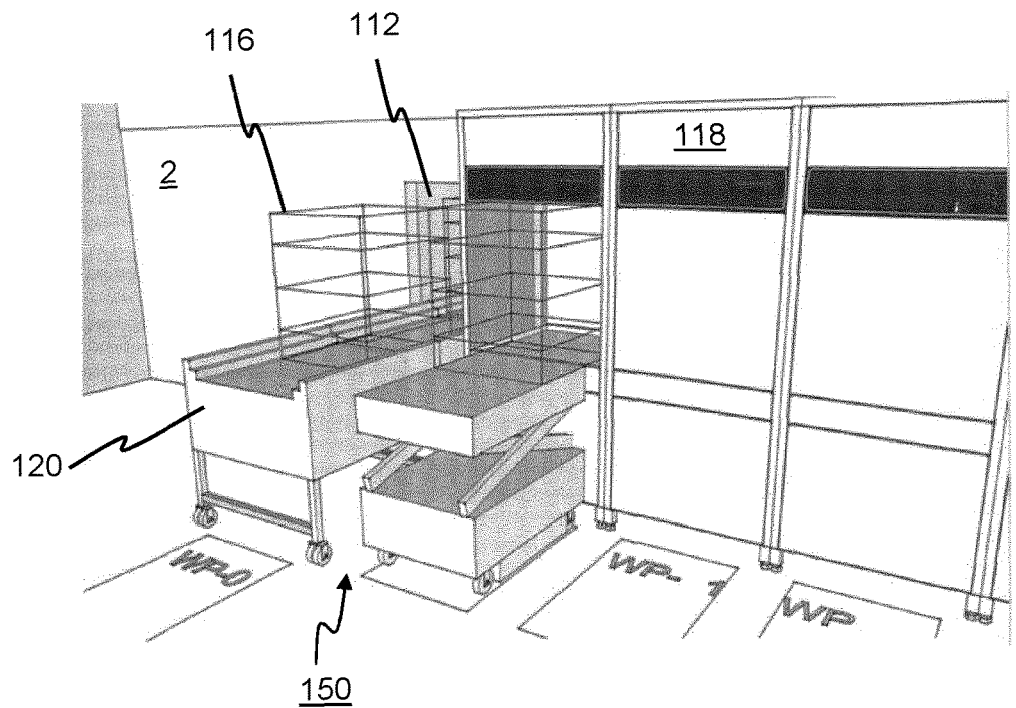
Figure 3C:
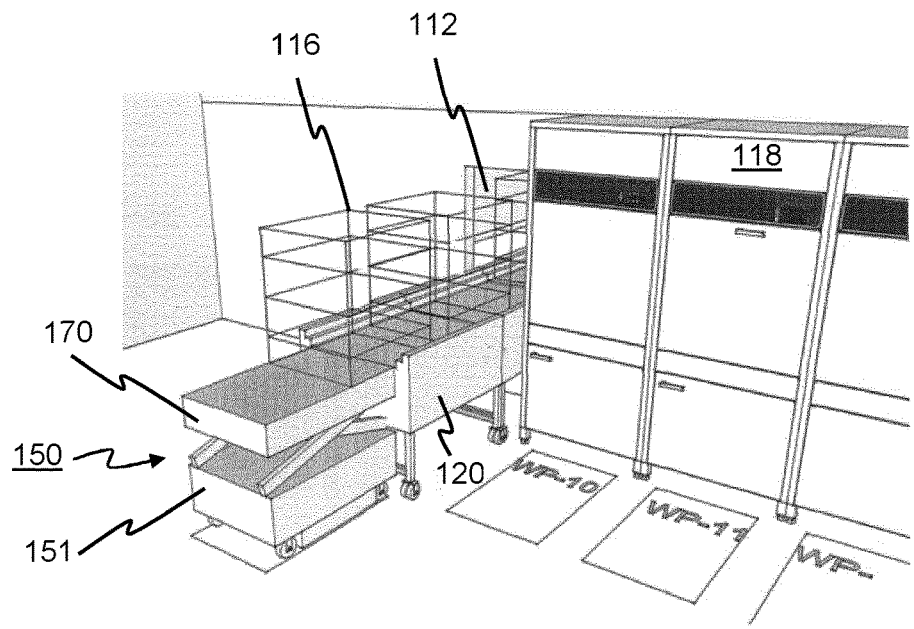

The vehicle 150 without basket may then move to a pick-up point WP-x at another table 115, if already summoned by an operator 101, or to another pick-up point WP-0, which may represent a waiting position, such as at a conveyor 120 at passage 112, see FIG. 3c, for either loading a clean basket 116 for subsequent delivery to a table 115 if so requested by an operator 101, or for moving—unloaded—from the waiting position WP-0 to a table 115 when so requested to, in order to move another filled basket 116 from that table 115 to a washer 118, as discussed above.

Figure 4B:
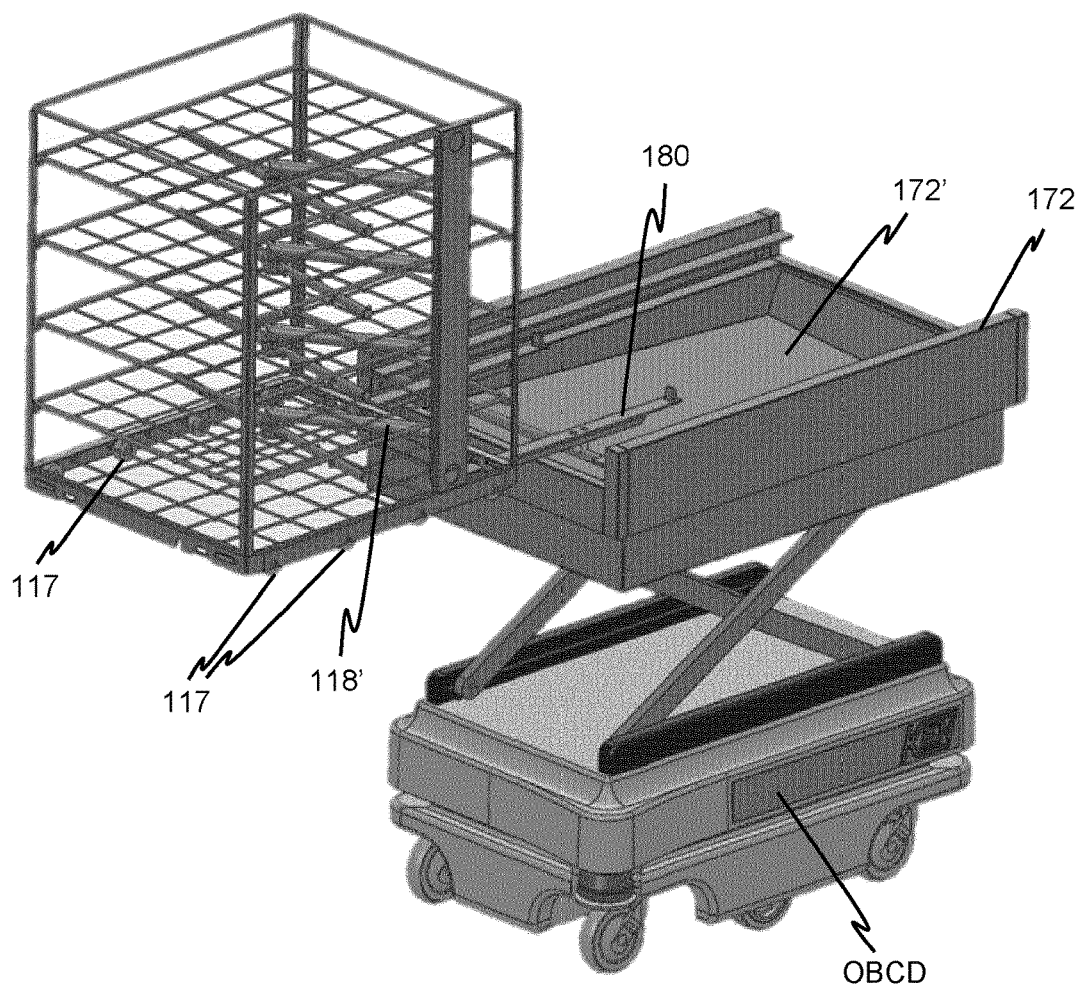

The basket shifting device of each vehicle 150 may in a highly simple embodiment schematically shown in FIG. 4b comprise telescopically operating arms 180 having a hook-like member 181 at one end configured for movement into a position engaging a part of the baskets 116 to pull a basket 116 completely onto the support surface defined by the pan 172' of the loading platform structure 172 on operation of the arm 180; conversely, for unloading the basket 116 into the washer 118 as shown in FIG. 3b the arms 180 are extended whereupon the hook-like member disengages the basket 116. On the other hand, in the clean area C the basket shifting device 180 would operate to pull out the clean basket 116 with washed articles from the washer 118 by performing the aforementioned loading procedure. Means could be provided for release of the basket 116 in the event the basket 116 becomes inadvertently fixed or its removal from the washer is inadvertently impeded.

Figure 4C:
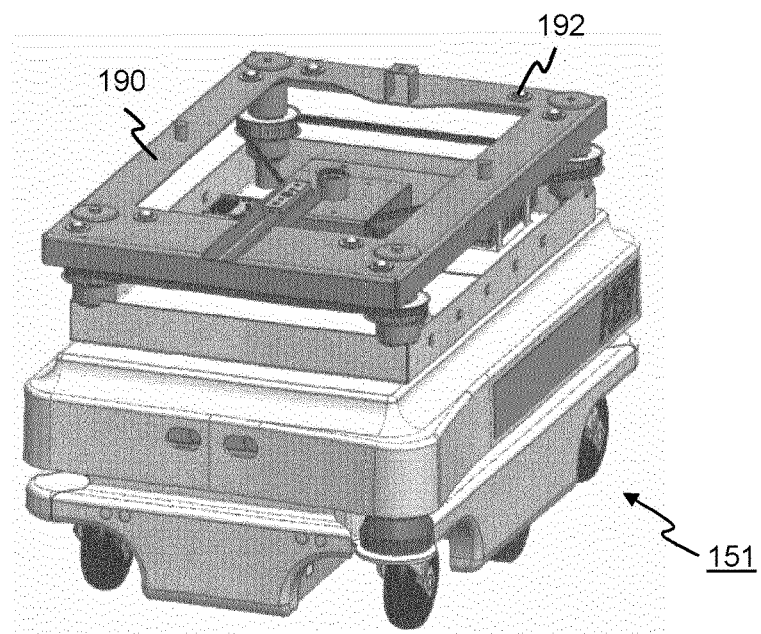
FIGS. 4c and 4d show an alternative mechanism using telescoping spindles/bars for raising the loading platform structure.
Figure 4D:
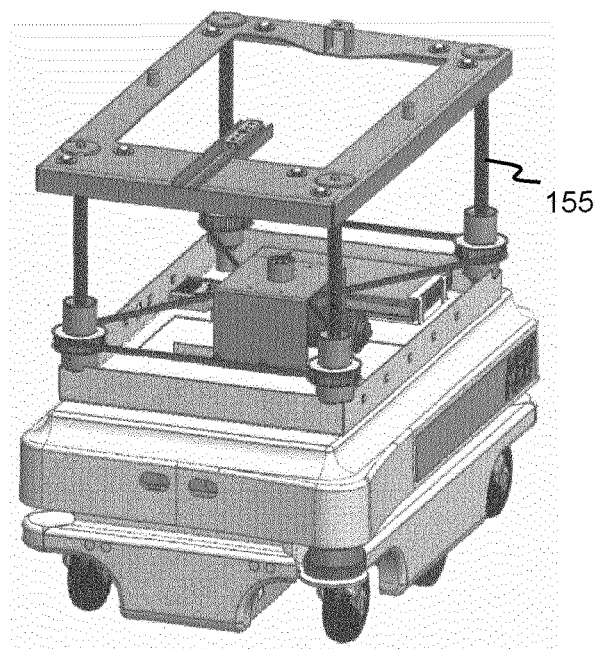

FIGS. 4c and 4d show an alternative mechanism 155 including telescoping spindles/bars for raising the loading platform structure 172.

Figure 5A:
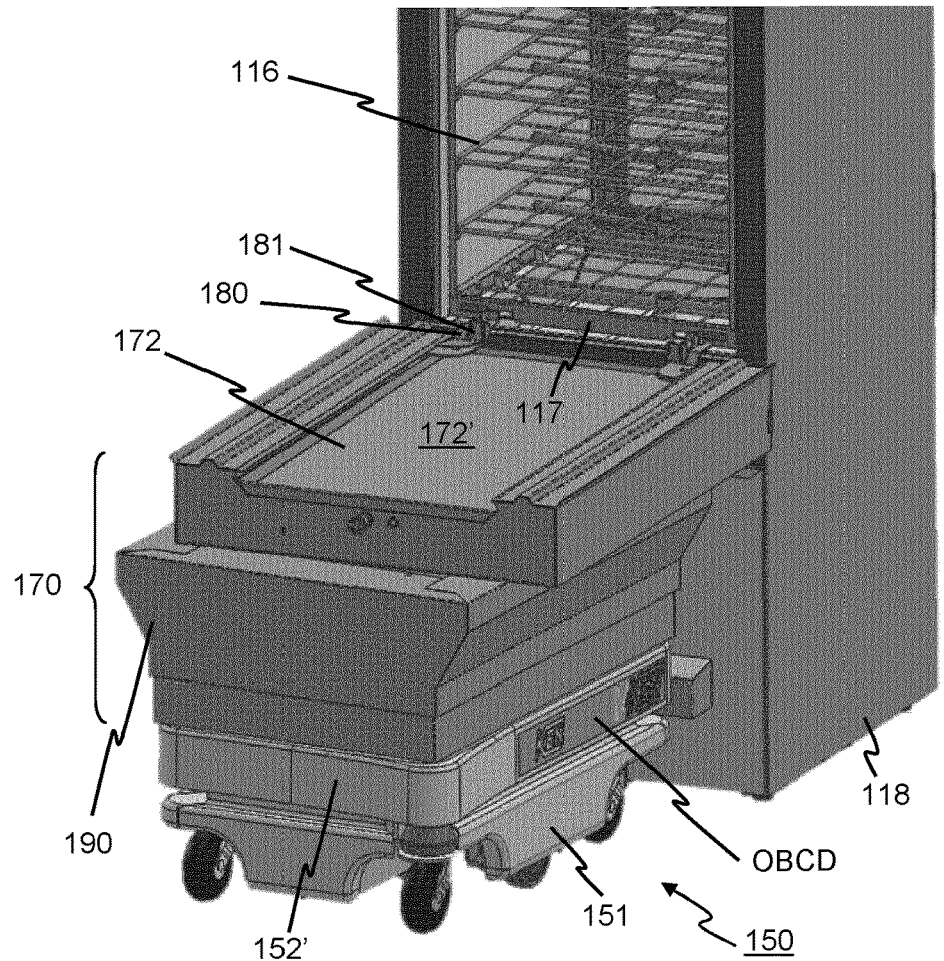
FIG. 5a shows in perspective view another embodiment of the facility of the invention, with a vehicle placed in front of a washer, for retracting a basket.
Figure 5B:
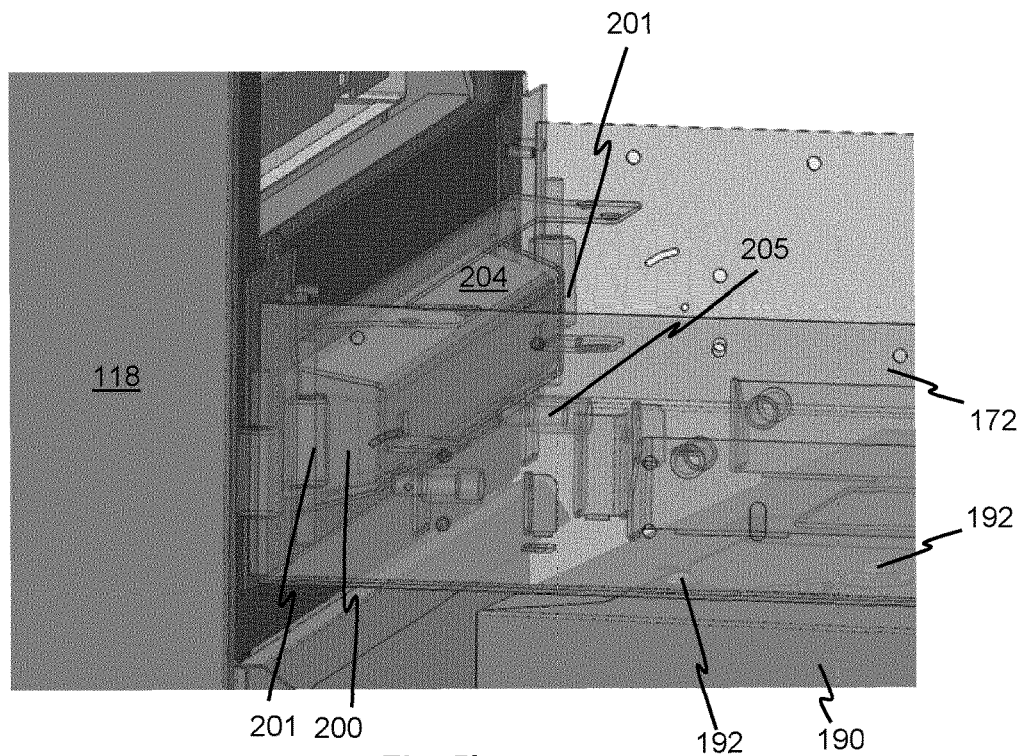
FIG. 5b shows a detail of the combination shown in FIG. 5a, FIG. 5c is a horizontal sectional view seen from above of the combination shown in FIG. 5a, and FIGS. 6a-6c are perspective detailed views showing a shifting device for the vehicle of the facility, in different configurations.

FIG. 5a shows a further embodiment of the invention, for allowing a highly exact docking of the vehicle 150 in alignment with the opening of inlet/outlet opening of a washer 118 to which the vehicle has travelled. This is particularly useful where the base 151 of the unmanned vehicle 150 may only be positioned relative to the washer 118 opening with a certain tolerance, such as with a lateral offset in the order of 10-20 mm, unless a time-consuming position-adjusting manoeuvring back and forth of the vehicle 150 is carried out. For this, the upper part 170 of the vehicle 150 in this embodiment comprises a separate bottom part 190, which preferably may be raised and lowered relative to the base 151 by an actuator as discussed above, supporting the loading platform structure 172. A carrier structure 192 between the bottom part 190 and the loading platform structure 170 with pan 172' is configured for allowing two-dimensional horizontal movements of the loading platform structure 172 relative to the bottom part 190 and, hence, relative to the base 151. FIG. 5b shows how the carrier structure in this embodiment comprises a plurality of roller bearings 192 distributed across the top of the bottom part 190. A system of springs 900 connected on the one hand to the bottom part 190 and on the other hand to the loading platform structure 172 may be provided and configured for controlling or limiting relative movements of the loading platform structure 172, as seen best in FIG. 5c.

Moreover, as shown in FIG. 5b, the washers 118 and the loading platform structure 172 in this further embodiment also comprise respective engagement devices 200, 201 for engaging each other, for an aligning of the loading platform structure 172, through the aforementioned horizontal movements, with the inlet opening of the washer 118. The engagement devices 200, 201 may, as shown in the view of FIG. 5b wherein certain structural parts are illustrated as being transparent for better visibility of other parts, comprise a pair of slanted vertical faces 200 at each end of a projecting bar 204 mounted to the front of the washer below the washer 118 opening and cooperating with a pair of rollers 201 mounted to the loading platform structure 172 above the front end 152 of the base 151 to rotate about a respective vertical axis. In the example of FIG. 5a the vehicle 150 has reached the opening of the washer 118 in a position with the base 151 at a small angle to the front of the washer 118 and the engagement devices 200, 201 have engaged each other and brought about the required alignment after the loading platform structure 172 has been moved relative to the bottom part 190 towards the front of the washer 118, as explained below. As the loading platform structure 172 is moved one of the pair of rollers 201 engages one of the pair of slanted faces 200, bringing about the alignment of the loading platform structure 172 with the washer 118 front, i.e. with the feed direction of baskets 116 into the washer 118, possibly through rotation of the structure 172 by combined horizontal movement in two perpendicular directions, with finally both slanted faces 200 contacting one of the rollers 201. The engagement devices 200, 201 for performing this alignment could be made in many different ways, such as my mounting the bar 204 on the vehicle 150 and the rollers 201 on the washer 118. Rotatable hooks 205 or other locking devices may be provided on the loading platform structure 172 and configured for physically engaging complementary locking devices on the washer 118, such as on the projecting bar 204, for temporarily maintaining the position of the loading platform structure 172 until the vehicle 150 has completed removal from the washer 118 or insertion into the washer 118, of a basket 116, at which point the vehicle 150 follows instructions for a path to be followed stored in the on-board control device OBCD.

The aforementioned relative movement of the loading platform structure 172 carrying the pan 172' is explained in the following with reference to FIG. 5c which is a horizontal sectional view seen from above of the set-up shown in FIG. 5a, with the pan 172' removed and with a basket engaging end (not shown) of a shifting device 180 engaging a basket (not shown) inside the washer 118, which is only schematically shown. In this embodiment a linear actuator 220 is rotatably connected at one end 222 with the loading platform structure 172 and at another end 221 with the bottom part 190. Respective aligners 230, 240 are provided for engaging each other through a wedge-like action when the linear actuator 220 is in a first configuration (see FIG. 6a), for locking the loading platform structure 172 in a fixed position relative to the bottom part 190. In this embodiment two symmetrically located pairs of aligners each comprise a pin 230 mounted to the bottom part 190 to project upwards into a corresponding opening 240 formed in a bottom plate of the loading platform structure 172 and defined by edges meeting at an apex of the opening 240. The openings 240 are shaped to provide sides along which the pins 230 may ride as the loading platform structure 172 moves relative to the bottom part 190, to define limits to the movement of the loading platform structure 172 relative to the bottom part 190. The relative movement referred to is initiated by activation of the linear actuator or similar structure 220 which at first advances the loading platform structure 172 carried by the carrier structure/ball bearings 192 in the straight line direction identified by letter A in FIG. 5c, until the engagement devices 200, 201 engage each other at which point the loading platform structure 172, being advanced by the actuator 220 and now being guided by the engagement devices 200, 201 riding on each other, normally will rotate relative to the bottom part 190 in case of misalignment with the washer 118, the actuator 220 now rotating at the two opposite ends 221, 222 thereof, for the aforementioned aligning of the loading platform structure 172 with the washer 118.

Figure 5C:
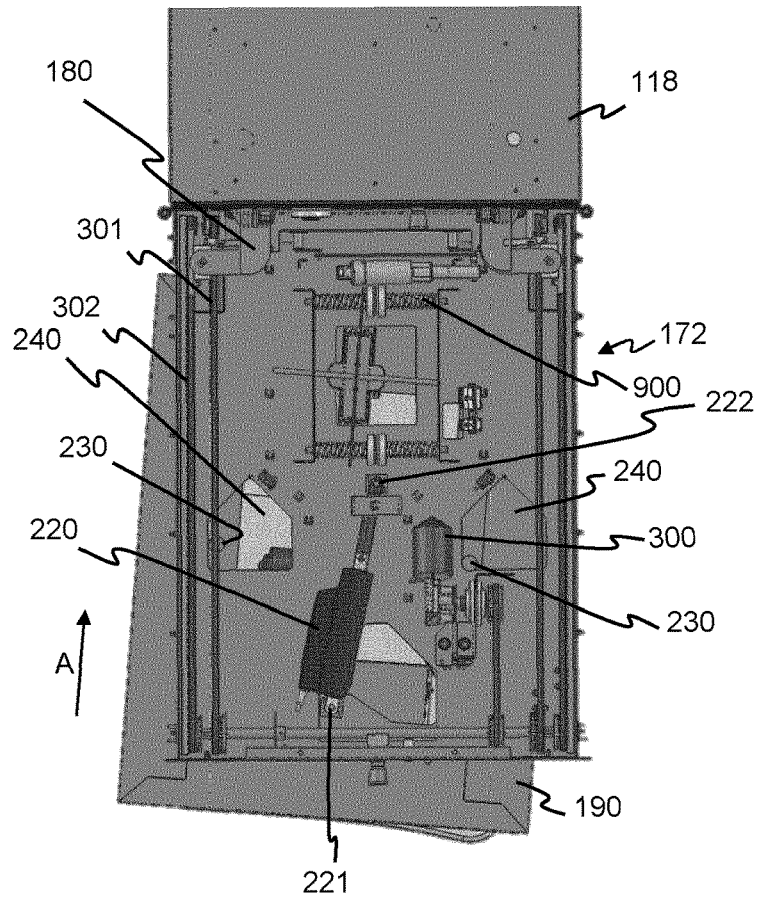

In a second, more extended configuration of the linear actuator 220 shown in FIG. 5c is the loading platform structure 172 now fully aligned with the opening of the washer 118, at which point sensors activate loading or unloading of a basket 116 using a shifting device 180 to be discussed in the following. After completion of the unloading or loading is the actuator 220 brought into its first non-extended configuration shown in FIG. 6a wherein the pins 230 are fixed relative to the respective opening 240 by being received at the aforementioned apex, with the loading platform structure 172 now aligned with the base 151.

Figure 6A:
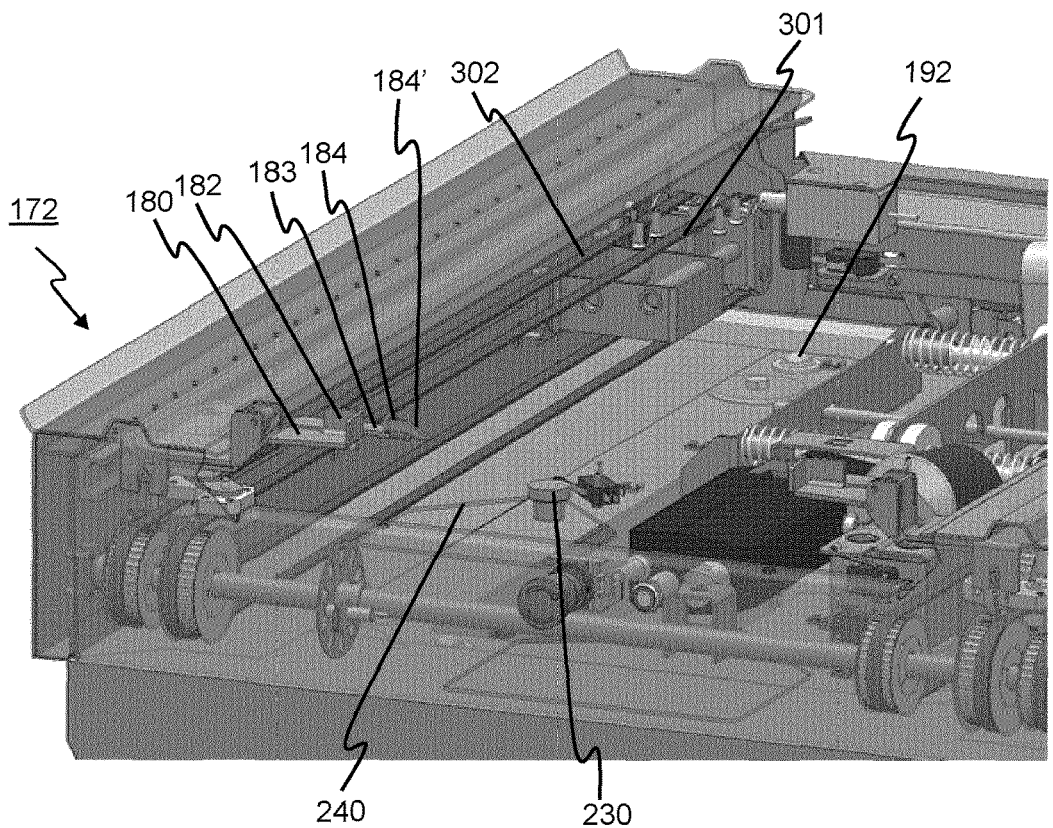

An embodiment of the shifting device will now be discussed with reference to FIGS. 6a-6d showing this embodiment used in the context of the vehicle 150 described with reference to FIG. 5a. In this alternative embodiment the shifting device includes an arm 180 movable along a first side of the loading platform structure 172 and rotating as this translational movement takes place, between a first position with a basket engaging end 181 of the arm 180 extending above the loading platform structure 172, as shown in FIG. 6a, to a second rotated position shown in FIG. 6b with the basket engaging end 181 located beyond the loading platform structure 172, i.e. projecting beyond the front end 152 of the base 151, either inside the washer 118 shown in FIG. 5a or over the upper surface of the pre-processing station 115, as in FIG. 3a.

For the movement of the arm 180 along the side of the loading platform structure 172 a single drive 300 is preferably used, being operatively connected with two belts or chains 301, 302, one 301 of the belts or chains operated for running at a higher speed than the other 302, for rotating the arm 180 from the position shown in FIG. 6a. This is achieved in the shown embodiment in that a driving wheel connected to the drive 300 axle on the one hand and driving belt 301 on the other hand has a larger diameter than another driving wheel connected to the drive 300 axle on the one hand and driving belt 302 on the other hand. A carriage 185 (see FIG. 6c) connected to belt 302 supports and advances the arm 180 along the first side of the loading platform structure 172, with the arm 180 pivotally connected to the carriage 185 at pivot point 186. A pin 187 carried by the other belt 301 connects with and rotates the arm 180 about pivot point 186 into the second position of the arm 180 shown in FIGS. 6b and 6c, by the movement of the pin 187 relative to the carriage 185 whereby the pin reaches the end of its translation slightly ahead of the carriage 185. Returning the carriage 185 and the pin 187 to the retracted second position of the arm 180 shown in FIG. 6a brings about a counter rotation of the arm 180.

Figure 6B:
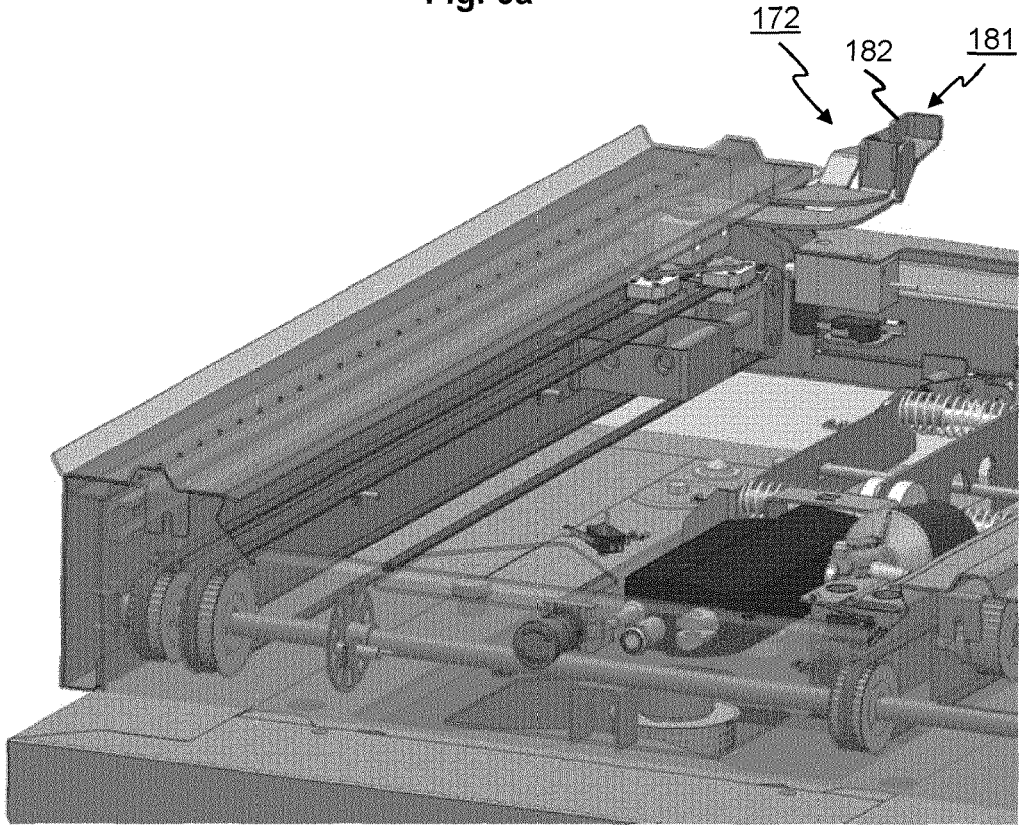
Figure 6C:
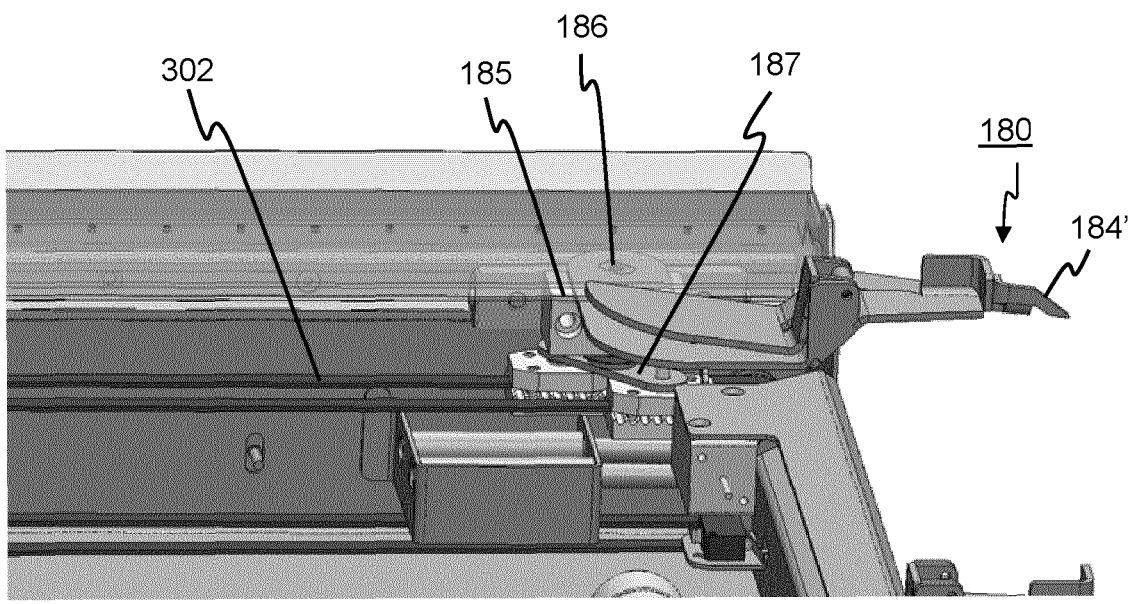

The arm 180 generally includes at the free end 181 various structural components for selectively engaging an inner face or an outer face (oriented to the outside of the basket 116) of a cross-bar 117 of the basket 116, depending on the arm 180 being used i) to pull a basket 116 onto the pan 172' from a washer 118 or from the top surface of a station 115 or ii) to push a basket 116 fully into a washer 116 or fully onto the top surface of a station 115. For pushing operations the arm 180 is at first in the position shown in FIG. 6a where a flange 182 of the arm 180 may engage an outer face of the cross-bar 117 of a basket 116 (not shown) on the pan 172' to push the basket 116 as the arm translates and rotates until the arm 180 assumes the rotated position shown in FIG. 6b where the basket 116 and the end 181 is located inside the washer 118, beyond the loading platform structure 172 adjacent the front end 152 of the vehicle 150. Returning the arm 180 to its initial position shown in FIG. 6a leaves the basket 116 behind in the washer 118. The cross-bar 117 is illustrated in FIG. 5a.

Where the vehicle 150 is to pull a basket 116 onto the pan 172', after the vehicle 150 has been correctly aligned with the washer 116 or station 115 the arm 180 is first moved to the position shown generally in FIG. 6b. For pulling operations the free end 181 of the arm 180 is configured for engaging the inner face of the cross-bar 117 of the basket 116. For this the end 181 of the arm 180 includes a pivotable sub-arm 183 with a vertical flange 184 for the engagement with the aforementioned inner face and having a ramp 184'. The sub-arm 183 is normally biased towards the position shown in FIGS. 6a and 6c but where movement of the arm 180 to the position shown in FIG. 6b brings the tip of the sub-arm 183 into contact with a basket 116 cross-bar 117 the sub-arm 183 will pivot as the ramp 184' rides on a lower face of the cross-bar 117, until the ramp 184' has moved past the cross-bar 117, at which point the sub-arm 183 will swing back, now with its further vertical flange 184 contacting the inner face of the cross-bar 117. Sensors may be provided to verify the arm 180 is in engagement with the basket 116, at which point the drive 300 is activated to return the arm 180 and carriage 185 combination to the position shown in FIG. 6a, pulling the basket 116 onto the pan 172'.

It is noted that the aforementioned pick-up points, referenced in the drawings by letters WP-x, may be defined as areas wherein the vehicles may perform a predetermined movement, such as a turning movement, whereby the vehicles 150 is turned such that the font end 152 thereof faces away from the pre-processing stations defined by the tables 115.

As shown in FIG. 2c one or more further unmanned vehicles 150' are preferably in a similar manner requested to travel on the floor of the clean area C from the outlet opening/extraction doors of the washers 118 upon conclusion of a washing cycle, using third type control devices 105' (not shown in details) also allowing manual input of requests by the operators 101 and located at the processing stations 115" in the clean area C.

The invention claimed is:

1. A processing facility for dirty medical articles, said processing facility comprising:
    a dirty facility area (D) and an adjacent clean facility area (C);
    baskets for receiving said dirty medical articles; and
    a wall (W) separating said dirty facility area (D) from said clean facility area (C), said dirty facility area (D) comprising:
        an entry door for receiving said dirty medical articles;
        pre-processing stations with tables for operator pre-washing/sorting of said dirty medical articles and for arranging pre-washed/sorted articles processed by said pre-processing stations in said baskets,
        pick-up points at said pre-processing stations for pick-up of said baskets with said pre-washed/sorted articles,
    a plurality of washers positioned along said wall (W), for washing said pre-washed/sorted articles arranged in said baskets, each of said plurality of washers comprising an inlet opening in said dirty facility area (D) and an outlet opening for washed articles in said clean facility area (C);

said clean facility area (C) comprising processing stations with tables for operator processing of said washed articles;

wherein
an unmanned vehicle configured for travelling on a floor of said dirty facility area (D) at least between said pick-up points (WP-x) and each of said inlet openings of said plurality of washers, said unmanned vehicle comprising:
a base with a front end and a rear end;
an upper part with a loading platform structure configured for supporting said baskets;
an on-board control device (OBCD) for receiving and executing mission information about a path of movement along which said unmanned vehicle should move;
each of said pre-processing stations comprising a first type control device for direct or indirect communication with said unmanned vehicle;
each of said plurality of washers comprising a respective second type control device for direct or indirect communication with said unmanned vehicle;
each first type control device being for calling said unmanned vehicle to said pick-up points (WP), said unmanned vehicle comprising sensors at said front end, for detecting obstacles along said path of movement across said floor.

2. The processing facility according to claim 1, comprising a second unmanned vehicle configured for travelling on said floor of said dirty facility area (D) at least between said pick-up points (WP-x) and each of said inlet openings of said plurality of washers.

3. The processing facility according to claim 2, each first type control device being for dispatching said unmanned vehicle from said pick-up points (WP).

4. The processing facility according to claim 1, each first type control device being for dispatching said unmanned vehicle from said pick-up points (WP).

5. The processing facility according to claim 1, said upper part comprising a bottom part supporting said loading platform structure, a carrier structure being configured for allowing relative horizontal movement of said loading platform structure with respect to said base.

6. The processing facility according to claim 1, comprising a main control unit for indirect communication of each of said plurality of washers with said unmanned vehicle, said unmanned vehicle receiving data representing information about a status of a washing cycle carried out, from each of said plurality of washers via said main control unit.

7. A method of processing dirty medical articles using a processing facility for dirty medical articles, the processing facility comprising:
a dirty facility area (D) and an adjacent clean facility area (C);
baskets for receiving said dirty medical articles; and
a wall (W) separating said dirty facility area (D) from said clean facility area (C), said dirty facility area (D) comprising:
an entry door for receiving said dirty medical articles;
pre-processing stations with tables for operator pre-washing/sorting of said dirty medical articles and for arranging pre-washed/sorted articles processed by said pre-processing stations in said baskets;
pick-up points at said pre-processing stations for pick-up of said baskets with said pre-washed/sorted articles;
a plurality of washers positioned along said wall (W), for washing said pre-washed/sorted articles arranged in said baskets, each of said plurality of washers comprising an inlet opening in said dirty facility area (D) and an outlet opening for washed articles in said clean facility area (C);
said clean facility area (C) comprising processing stations with tables for operator processing of said washed articles;

wherein
an unmanned vehicle configured for travelling on a floor of said dirty facility area (D) at least between said pick-up points (WP-x) and each of said inlet openings of said plurality of washers, said unmanned vehicle comprising:
a base with a front end and a rear end;
an upper part with a loading platform structure configured for supporting said baskets;
an on-board control device (OBCD) for receiving and executing mission information about a path of movement along which said unmanned vehicle should move;
each of said pre-processing stations comprising a first type control device for direct or indirect communication with said unmanned vehicle;
each of said plurality of washers comprising a respective second type control device for direct or indirect communication with said unmanned vehicle;
each first type control device being for calling said unmanned vehicle to said pick-up points (WP), said unmanned vehicle comprising sensors at said front end, for detecting obstacles along said path of movement across said floor, wherein said method comprising:
inputting a request into said first type control device arranged at one of said pre-processing stations to summon said unmanned vehicle of said dirty facility area (D) to arrive into a position at an adjacent one of said pick-up points (WP-x), receiving data representing information about a status of a washing cycle carried out by the respective plurality of washers, shifting one of said baskets containing dirty medical articles to be washed to said loading platform structure of said unmanned vehicle arrived at said one of said pick-up points (WP-x); and
directing said unmanned vehicle towards one of said washers, which is either ready to receive said one of said baskets containing dirty medical articles a for washing, or which first will be ready to receive said one of said baskets containing dirty medical articles, based on said received data representing information.

8. The method according to claim 7, wherein said unmanned vehicle is instructed to then move to a second one of said pick-up points (WP-x) at another one of said pre-processing stations, if already summoned, or to a third one of said pick-up points (WP-0) representing a waiting position for loading a clean basket for subsequent delivery to said another one of said pre-processing stations if so requested.

9. The method according to claim 8, comprising operating a shifting device to engage one of said baskets to pull said one of said baskets from said one of said pre-processing stations and completely into a position supported fully and stable by said loading platform structure.

10. The method according to claim 7, comprising operating a shifting device to engage one of said baskets to pull said one of said baskets from said one of said pre-processing stations and completely into a position supported fully and stable by said loading platform structure.

11. The method according to claim 10, comprising operating said shifting device to engage one of said baskets to unload said one of said baskets from said loading platform structure into a position supported fully by said one of said washers.

\* \* \* \* \*